United States Patent [19]

Oh

[11] 4,437,193
[45] Mar. 20, 1984

[54] PROTRUSIO CUP

[76] Inventor: Indong Oh, 851 Lyndon St., South Pasadena, Calif. 91030

[21] Appl. No.: 340,024

[22] Filed: Jan. 18, 1982

[51] Int. Cl.$^3$ .............................................. A61F 1/04
[52] U.S. Cl. ................................... 3/1.912; 128/92 C
[58] Field of Search ........................... 3/1.912, 1.913; 128/92 C, 92 CA

[56] References Cited

U.S. PATENT DOCUMENTS

| D. 235,377 | 6/1975 | Medcraft | D83/1 E |
| 2,947,308 | 8/1960 | Gorman | 128/92 EA |
| 3,840,904 | 10/1974 | Tronzo | 3/1.912 |
| 3,903,549 | 9/1975 | Deyerle | 3/1 |
| 3,918,102 | 11/1975 | Eichler | 3/1.912 |
| 4,262,369 | 4/1981 | Roux | 128/92 CA |
| 4,327,449 | 5/1982 | Charnley | 3/1.912 |

OTHER PUBLICATIONS

Harris, et al., "Oh–Harris Protrusio Shell Surgical Technique", Howmedica Surgical Technique, Dec. 1979, pp. 1–6.

*Primary Examiner*—Richard J. Apley
*Assistant Examiner*—David J. Isabella
*Attorney, Agent, or Firm*—Gordon L. Peterson

[57] ABSTRACT

A protrusio cup comprising an acetabular cup and a protrusio shell mounted on the acetabular cup so that the protrusio cup can be implanted as a unit. The protrusio shell has three flanges for engaging the ilium, ischium and pubis, respectively. The acetabular cup has an extension in at least the superior-posterior region to reduce the likelihood of dislocation.

18 Claims, 6 Drawing Figures

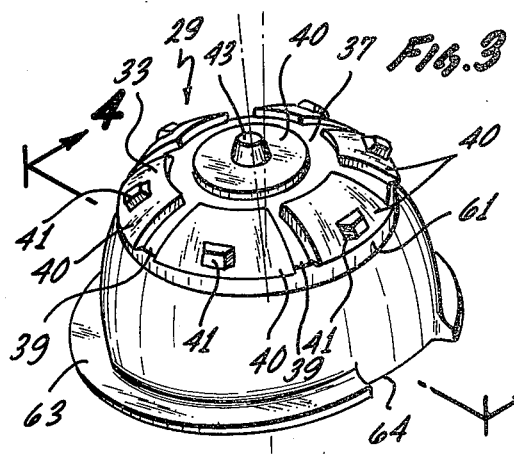
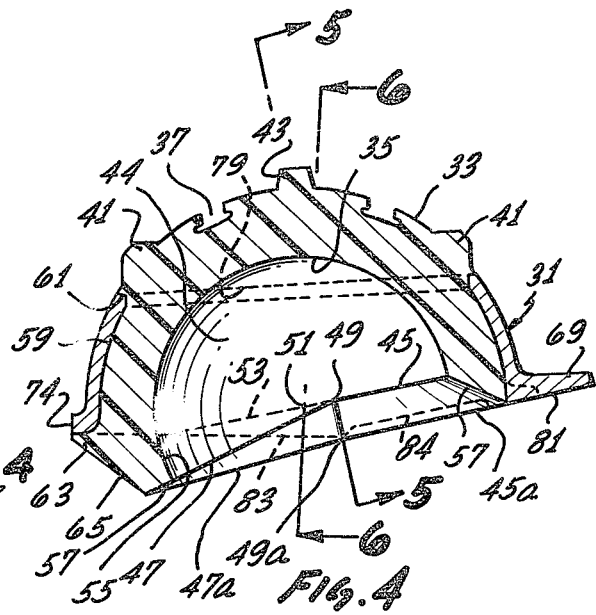
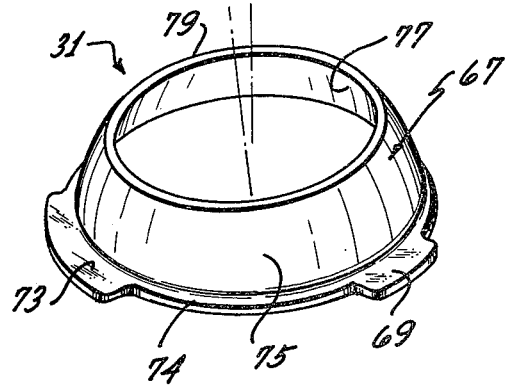
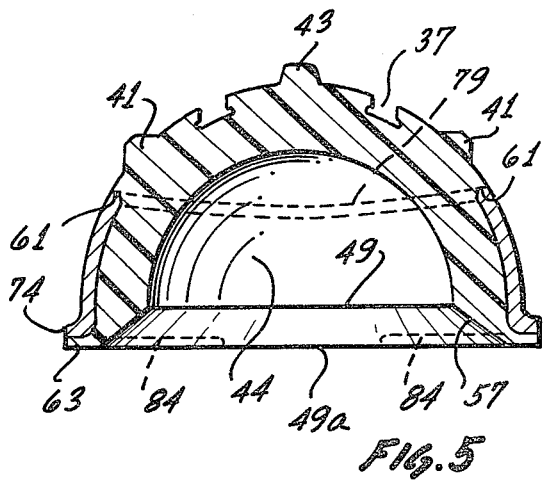
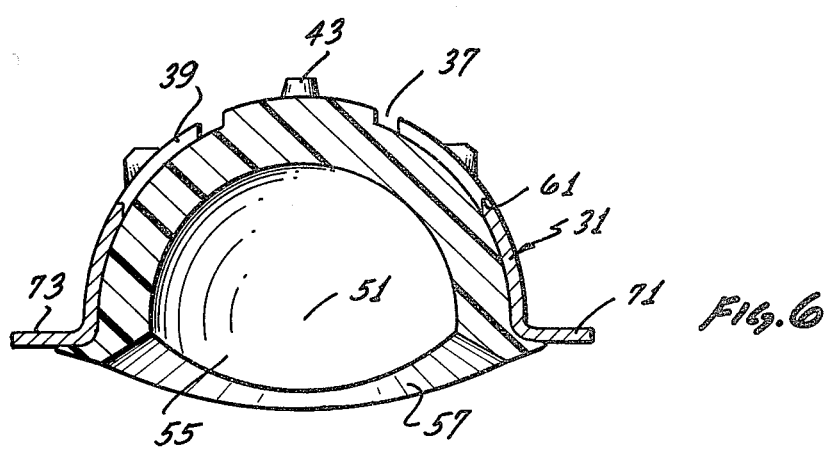

PROTRUSIO CUP

BACKGROUND OF THE INVENTION

A hip joint comprises a socket or acetabulum and a femoral head or ball received in the acetabulum. Thus, the hip joint is a ball and socket joint which provides universal motion.

Various diseases, such as osteoarthritis attack the hip joint and, when this occurs, it may be necessary to utilize an appropriate hip joint prosthesis to replace the femoral head and the acetabulum. This may also be necessary in other circumstances such as in the case of certain hip joint fractures.

Deterioration of the acetabulum requires that an acetabular cup be mounted in the acetabulum to provide a socket for slidably receiving the prosthetic femoral head. If the medial wall of the acetabulum is sufficiently weakened, it may be necessary to protect this wall with a protrusio shell. The protrusio shell has one or two flanges for seating on the ilium, the ischium and the pubis. Accordingly, the medial thrust from the femoral head is transferred away from the medial wall through the flanges to the ilium, ischium and pubis.

During surgery, the protrusio shell is cemented into the acetabulum, and immediately thereafter, the acetabular cup is cemented into the acetabulum and within the protrusio shell. Unfortunately, the surgical requirements for separately placing of these two components is quite complex, and it is difficult to achieve the proper positioning of both of these components relative to each other.

The flanges of the protrusio shell, while necessary to achieve the desired force transfer, also tend to interfere with various functions of the hip joint. It is known to provide the flange in two segments, one for the iliac and ischial acetabular rim and the other for the pubic segment of the acetabular rim. One of these spaces between these two segments permits the psoas tendon to glide freely back and forth as it enters the thigh and the other space between the segments eliminates contact between the femoral neck and the flange.

Another problem with hip joint prostheses is dislocation, i.e., removal of the femoral head from the acetabular cup. Some dislocations can be forced back into position by manipulation of the leg under anesthesia and others require open surgery. In either event, a dislocated hip is quite painful.

The segment of the flange between the ilium and the ischial areas creates a likelihood of grinding of the femoral head against the exposed flange in case of dislocation of the hip joint. During relocation of a dislocated hip, the femoral head may hook this flange and cause loosening of the cup.

In an effort to avoid dislocation, it is known to provide an acetabular cup which has straight tangent sections which extend past the hemisphere. Unfortunately, when a hip joint prosthesis of this type dislocates, it usually requires open surgery in order to be placed back into position.

An obvious approach to the dislocation problem would be to extend the acetabular cup far enough past the hemisphere to lock over the femoral head. This would lock the femoral head within the acetabular cup with a snap action which would tend to deter dislocation. Unfortunately, it is necessary that the femoral head be relatively easily removable from the acetabular cup because, if it is not, a dislocation could pull out the acetabular cup from the acetabulum. Accordingly, there is a need for a hip joint prosthesis that will effectively retard dislocation without incurring risk of substantial damage due to forceable removal of the acetabular cup.

SUMMARY OF THE INVENTION

This invention is directed toward solving the problems discussed above. For example, this invention provides a protrusio cup which includes an acetabular cup and a protrusio shell with the protrusio shell mounted on the acetabular cup. Accordingly, the protrusio cup can be implanted as a single unit in a one-step surgical technique. Because the protrusio shell is mounted on the acetabular cup, the orientation of these two components relative to each other is predetermined, and the operative procedure is speeded up.

Another feature of the invention is that the shell may have three flanges for engagement with the ilium, ischium and pubis, respectively. The absence of any flange between the ilium and ischial areas avoids any possible grinding of the femoral head against the flange in the case of dislocation of the hip joint. Also, during relocation of the hip joint, the likelihood of loosening of the protrusio cup is reduced.

To match the contour of the rim of the acetabulum, the flanges which engage the ilium and ischium are in the same plane and the flange which engages the pubis is in a different plane. For anatomical reasons, this latter flange is also the shortest circumferentially.

Dislocation of a hip joint prosthesis frequently occurs as a result of forces which remove the femoral head from the acetabular cup in the superior-posterior region. To help prevent dislocation, the acetabular cup has an overhanging portion or extension at least in the superior-posterior region. Preferably, the overhanging portion extends beyond the superior-posterior region to help avoid dislocation and to provide symmetry; however, the overhang should not extend for a full 360°. This extension also provides a secure roof or bearing surface for the articulating movement of the femoral head.

The acetabular cup is of approximately hemispherical configuration and has an outer surface with a generally part spherical contour. The acetabular cup also has an inner concave bearing surface of part spherical configuration adapted to receive the femoral head.

The extension is not simply the result of providing a bearing surface which is larger than hemispherical. Rather, the overhang or extension is provided in the region where it will be effective in reducing the likelihood of dislocation. This can be accomplished by causing the bearing surface to terminate in an edge lying in first and second planes which intersect along a line to define an obtuse angle which opens outwardly of the cavity. An extension of the first plane through the line of intersection and across the bearing surface divides the bearing surface into an approximately hemispherical portion on one side of the first plane and a bearing surface extension on the other side of the plane, which is preferably part spherical to provide maximum support for the femoral component. Thus, the bearing surface extension lies between the second plane and the extension of the first plane. With this construction, the acetabular cup extends beyond the hemisphere only along the second plane and not along the first plane. Accordingly, the femoral head is not so tightly retained within the cup that a dislocation would pull the cup from the acetabulum.

When the acetabular cup is used with a protrusio shell, the extension or overhang of the cup protrudes beyond the protrusio shell. Preferably, the line of intersection referred to above is offset from the center of the bearing surface. The acetabular cup has a sloping surface joining a portion of the inner bearing surface to a portion of the outer surface. The sloping surface provides the maximum potential range of motion.

The outer surface of the acetabular cup preferably has grooves defining segments on the outer surface of the cup. In use of the acetabular cup, the cement interlocks with the surfaces defining these grooves to provide an interlock between the cement and the cup. To increase the strength of this interlock, one or more of the grooves is preferably undercut to define a flange. This enables some of the cement to extrude beneath the flange to increase the strength of the interlock and to tend to resist removal of the acetabular cup from the acetabulum.

The outer surface of the acetabular cup has pods or spacer lugs which are engageable with the surface of the acetabulum to assist in positioning the cup within the acetabulum. This assures that substantially equal thicknesses of cement will exist along the outer surface of the acetabular cup and helps assure a more uniform load transfer to the bone while minimizing the likelihood of eccentric placement of the cup.

It is desirable to have the wall thickness of the cup be substantially uniform, except, of course, for the presence of the grooves and lugs. This can be advantageously accomplished by making the bearing surface and the outer surface substantially concentric. If these two surfaces were non-concentric, the wall thickness of the cup would vary throughout the cup, and this increases the likelihood that differential stress distribution would loosen the cup from the acetabulum.

The invention, together with additional features and advantages thereof, may best be understood by reference to the following description taken in connection with the accompanying illustrative drawing.

BRIEF DESCRIPTION OF THE DRAWING

FIG. 3 is an exploded perspective view of the protrusio cup.

FIG. 4 is a sectional view taken generally along line 4—4 of FIG. 3.

FIGS. 5 and 6 are sectional views taken generally along lines 5—5 and 6—6, respectively, of FIG. 4.

DESCRIPTION OF THE PREFERRED EMBODIMENT

Figure 1:
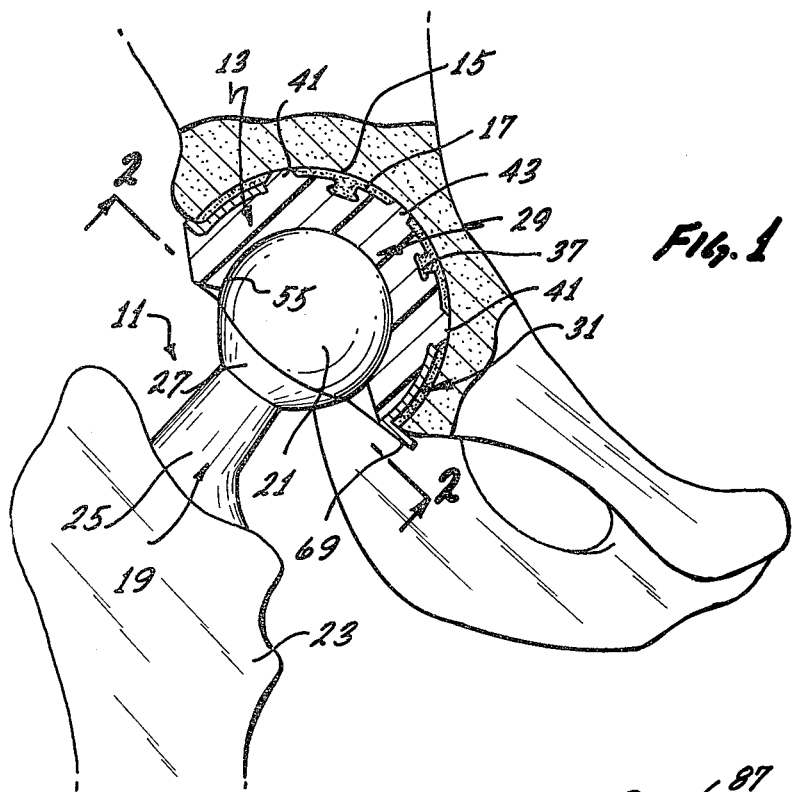
FIG. 1 is a front elevational view partially in section showing a hip joint prothesis for the right hip which includes one preferred embodiment of the protrusio cup of this invention.

FIG. 1 shows a hip joint prosthesis 11 which includes a protrusio cup 13 retained in the acetabulum 15 by bone cement 17 and a femoral component 19 having a femoral head 21 slidably received within the protrusio cup 13. The protrusio cup 13 can be used with femoral components of various different constructions. The femoral component 19, which is shown by way of example, also comprises a stem (not shown) which is inserted into the femur 23 and a neck 25 for joining the femoral head 21 to the stem. The femoral head 21 is essentially spherical, except for one or more conical portions 27 adjacent the neck 25.

The protrusio cup 13 comprises an acetabular cup 29 and a protrusio shell 31. The acetabular cup 29 is preferably molded of a suitable biocompatible plastic material, such as polyethylene. Although the acetabular cup 29 is of approximately hemispherical configuration, it is, in the preferred embodiment, not geometrically hemispherical in that, as set forth more particularly hereinbelow, it extends for more than 180° on one side and its outer surface is irregular. Although the acetabular cup 29 of this invention is particularly adapted for use with the protrusio shell 31, it can be used without a protrusio shell or with protrusio shells other than the shell 31.

The acetabular cup 29 has an outer surface 33 with a generally part-spherical contour and an inner concave bearing surface 39 of part-spherical configuration adapted to receive the femoral head 21. The surfaces 33 and 35 are concentric. To provide a better interlock with the cement 17, the outer surface 33 is preferably of irregular configuration and for this purpose has an annular latitude groove 37 (FIG. 3) and a plurality of longitude grooves 39 which intersect the latitude groove to define segments 40 (FIG. 3). A plurality of pods of spacer lugs 41 is arranged in a ring with each of the lugs 41 being on a segment 40 intermediate an adjacent pair of the longitude grooves 39. In addition, a spacer lug 43 is provided on a segment 40 coaxially with the annular latitude groove 37.

As shown in FIG. 1, these lugs 41 and 43 engage the wall of the acetabulum 15 to provide an even thickness of the cement 17. In addition, the spacer lugs transfer force to the bone and aid in properly positioning of the protrusio cup 13 within the acetabulum 15.

The acetabular cup 29 defines a cavity 44 which opens at a mouth. As best shown in FIGS. 1,2,4 and 6, the bearing surface 35 terminates in a free edge which lies in planes 45 and 47 which intersect along a line 49 to define an obtuse angle which opens outwardly of the cavity 44. Although different angles can be used, in the embodiment illustrated, the obtuse angle is 165°. As shown in FIG. 4, the line 49 is spaced from the center 51 of the outer surface 33 and the bearing surface 35. An extension of the plane 45 along dashed line 53 extends through the center 51 and divides the bearing surface 35 into a hemispherical 180° portion on one side of the plane 45 and a part-spherical bearing surface extension 55 on the other side of the plane 45 and between dashed line 53 and the second plane 47. In the embodiment illustrated, the angle defined by the plane 47 and the dashed line 53 is 15° and this is the preferred angle.

When the cavity 44 receives the femoral head 21, the plane 45 lies generally along the equator of the femoral head. However, the plane 47 lies below the equator. In other words, the bearing surface extension 55 forms a sector of a sphere which extends beyond the hemisphere but only on one side of the line 49. For this reason, the ability of the acetabular cup 29 to grip the femoral head 21 is much less than if the entire edge of the cavity 44 extended beyond the hemisphere of the femoral head.

The outer surface 33 terminates in a free edge which lies in planes 45a and 47a which intersect at a point 49a to define an angle which is only slightly less than 180° and which opens outwardly. The planes 45 and 45a are parallel. The lines 49 and 49a define the cutting plane 5—5 which is perpendicular to the plane 45.

The acetabular cup 29 has a sloping surface 57 which leads from the bearing surface 39 radially outwardly to allow the maximum potential range of motion. A portion of the sloping surface 57 lies within the plane 47.

Although the protrusio shell 31 can be mounted in different ways on the acetabular cup 29, in the embodiment illustrated, the cup has an annular groove 59 for receiving the protrusio shell. The groove 59 is defined by a shoulder 61 along one circumferential edge and a circumferentially extending flange 63 along the other circumferential edge. The shoulder 61 is interrupted by the longitude grooves 39 (FIG. 3). The flange is discontinuous and defines a radial gap 64 (FIG. 3). As shown in FIG. 4, an outer sloping surface 65 extends from the flange 63 to the sloping surface 57 in the region of the bearing surface extension 55. Thus, the bearing surface extension 55 is formed on an extension of the acetabular cup 29 which projects beyond the groove 59.

The protrusio shell 31 is preferably integrally constructed of a suitable biocompatible metal. The protrusio shell 31 comprises an annular segment 67 and three flanges 69, 71 and 73 projecting radially outwardly from the wide end of the annular segment. The flanges 69, 71 and 73 are spaced circumferentially by a radially short ledge 74 which extends continuously between the adjacent flanges. The centers of the flanges 69 and 71 are preferably equally spaced, and the radial dimension of the flange 69 is less than the radial dimension of the other two flanges. The radial dimensions of the flanges 71 and 73 are preferably equal. The annular segment 67 has a part spherical outer surface 75 and a concentric, part spherical inner surface 77. The protursio shell 31 is open at both ends.

The protrusio shell 31 has an edge 79 at one end and edges 81 and 83 at the other end. The edge 81 has two notches 84 (FIG. 5). The edge 81 (except for the notches 84) and the edge 83 lie in planes which intersect at the line 49a to define an obtuse angle which opens inwardly toward the cavity 44. The flange 69 lies in the same plane with the unnotched portion of the edge 81 and the flanges 71 and 73 lie in the same plane with the edge 83. The edge 79 is not parallel to either of the edges 81 or 83 in the embodiment illustrated.

Figure 2:
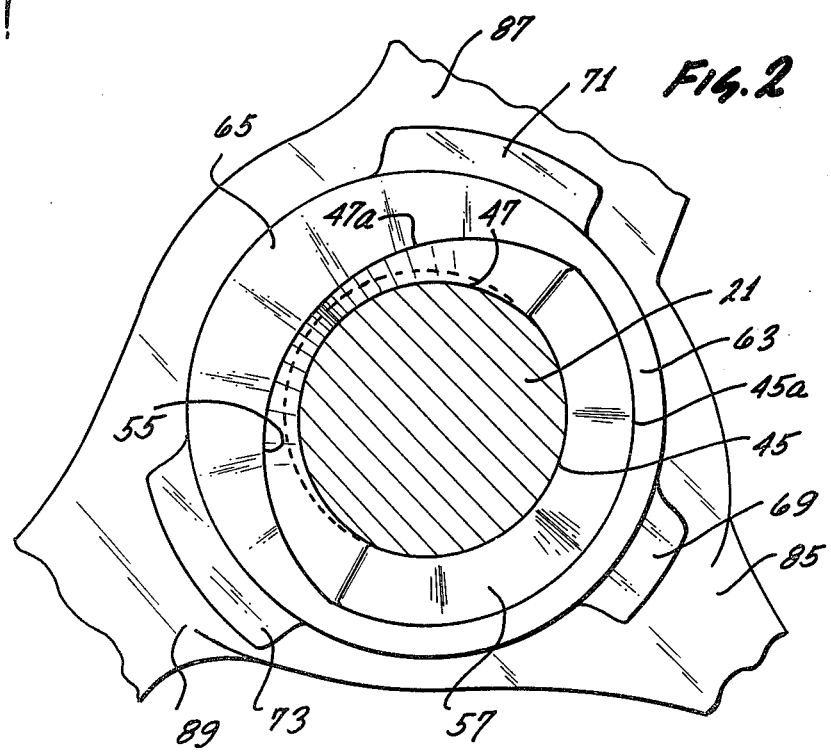
FIG. 2 is an enlarged fragmentary sectional view taken generally along line 2—2 of FIG. 1.

The protrusio shell 31 is mounted in the groove 59 of the acetabular cup during manufacture of the protrusio cup 13 or by the physician prior to surgery. The shell 31 is mounted snugly within the groove 59 with the ledge 74 and the flanges 71 and 73 resting on the flange 63 of the acetabular cup. The flange 69 is snugly received within the gap 64. As shown in FIG. 2, the flanges 71 and 73 project radially outwardly from the opposite ends of the bearing surface extension 55, and the flanges 71 and 73 are spaced apart circumferentially to provide a gap over the central region of the bearing extension surface 55.

When mounted in this manner, the plane 45a and the plane of the unnotched portion of the edge 81 are preferably substantially the same. The portion of the cup 29 which defines the bearing surface extension 55 is essentially not surrounded by the protrusio shell 31, and the bearing surface extension projects through the plane of the edge 83 of the protrusio shell. The annular edge 79 is skewed on the cup 29 in that a plane passing through the center 51 perpendicular to the plane of the edge 79 would not bisect the plane of the edge 79.

In use, the protrusio cup 13 can be implanted as a unit into the acetabulum 15, and this simplifies the operative procedure and eliminates the necessity of having to position the acetabular cup and the protrusio shell relative to each other. As shown in FIGS. 1 and 2, the bearing surface extension 55 lies primarily in the superior-posterior region and has its maximum extension posteriorly of the most superior position. For example, the maximum extension may be displaced 30° to 45° from the most superior position. When so positioned, portions of the bearing surface extension 55 are also in the superior-anterior and inferior-posterior regions as shown in FIG. 2. The flanges 69, 71 and 73 are spaced circumferentially so that they engage the pubis 85, ischium 87 and iliac respectively to transfer loads to the bony regions they engage. The absence of any flange between the ilium and ischium avoids grinding of the femoral head against such flange in case of dislocation.

Although an exemplary embodiment has been shown and described, many changes can be made by those skilled in the art without departing from the spirit and scope of the invention.

I claim:

1. A protrusio cup which can be implanted as a unit in the acetabulum comprising:
    an acetabular cup adapted to be received within the acetabulum;
    said acetabular cup having an inner concave bearing surface of generally part spherical configuration defining a cavity which opens at a mouth, said bearing surface being adapted to receive a femoral head and slidably cooperate therewith;
    said acetabular cup having an outer surface;
    a protrusio shell having a part spherical annular segment receiving a circumferentially extending annular region of the acetabular cup adjacent the mouth of the acetabular cup and flange means adjacent one end of the annular segment projecting generally radially of the annular segment and adapted to engage the bony region around the acetabulum, the other end of the annular segment of the protrusio shell being open with the acetabular cup extending through the opening;
    means for mounting the protrusio shell on the acetabular cup prior to implantation whereby the acetabular cup with the protrusio shell mounted thereon can be implanted as a unit in the acetabulum; and
    said mounting means including a circumferentially extending groove formed in the outer surface and lying entirely within the annular region of the acetabular cup which receives at least a portion of the annular segment of the protrusio shell.

2. A protrusio cup as defined in claim 1 wherein said acetabular cup has spacer lugs on the outer surface thereof engageable with the surface of the acetabulum to assist in positioning the protrusio cup in the acetabulum.

3. A protrusio cup as defined in claim 1 wherein said flange means includes first and second spaced flanges lying in different planes.

4. A protrusio cup as defined in claim 1 wherein said flange means includes first, second and third flanges spaced apart to engage the ilium, ischium and pubis, respectively.

5. A protrusio cup as defined in claim 4 wherein said first and second flanges are essentially co-planar and said third flange is in a plane forming an acute angle with the first and second flanges.

6. A protrusio cup as defined in claim 4 wherein said third flange is shorter circumferentially than either the first or second flanges.

7. A protrusio cup as defined in claim 1 wherein said bearing surface terminates in a free edge, first and second portions of said free edge lie in first and second planes, respectively, which intersect to form an obtuse angle which opens outwardly of said cavity.

8. A protrusio cup as defined in claim 1 wherein said protrusio shell terminates in an end edge at said one end of the annular segment with at least a portion of said end edge lying in a plane, said bearing surface having an extension that projects through said plane to define an overhang that resists dislocation of the femoral head.

9. A protrusio cup as defined in claim 1 wherein the acetabular cup is of approximately hemispherical configuration, said outer surface has a generally part-spherical contour, said bearing surface terminates in an edge lying in first and second planes which intersect along a line to define an obtuse angle which opens outwardly of the cavity, an extension of said first plane through said line and across the bearing surface dividing the bearing surface into an approximately hemispherical portion on one side of the first plane and a bearing surface extension on the other side of said first plane between said extension of the first plane and the second plane, said bearing surface and said outer surface being substantially concentric.

10. A protrusio cup as defined in claim 9 wherein said line is offset from the center of said bearing surface.

11. A protrusio cup as defined in claim 9 wherein said bearing surface extension is part spherical.

12. A protrusio cup as defined in claim 9 including spacer lugs on the outer surface engageable with the surface of the acetabulum to assist in positioning the acetabular cup in the acetabulum.

13. A protrusio cup as defined in claim 9 wherein said bearing surface extension forms a sector of a sphere which extends circumferentially of the acetabular cup for more than 180 degrees.

14. A protrusio shell comprising:
an annular segment having part spherical inner and outer surfaces with the inner part spherical surface defining a cavity which is open at both ends of the annular segment, said cavity being sized to receive an acetabular cup and the outer surface of the annular segment being adapted to be received in an acetabulum;
first, second and third flanges integral with the annular segment and projecting radially thereof adjacent one end of the annular segment; and
said first, second and third flanges having a length and orientation such that said first flange exclusively engages the ilium with respect to the ischium and pubis, the second flange exclusively engages the ischium with respect to the ilium and pubis and the third flange exclusively engages the pubis with respect to the ilium and ischium when the protrusio shell is implanted in the acetabulum.

15. A protrusio shell as defined in claim 14 wherein the circumferential dimension of the third flange is less than the circumferential dimension of the first and second flanges.

16. A protrusio shell as defined in claim 14 wherein the first and second flanges are in essentially the same plane and said third flange is in a plane different from the plane of the first and second flanges.

17. A protrusio cup comprising:
an acetabular cup adapted to be received within the acetabulum;
said acetabular cup having an inner concave bearing surface of generally part spherical configuration defining a cavity opening at a mouth, said bearing surface being adapted to receive a femoral head and slidably cooperate therewith;
said acetabular cup having an outer surface;
a protrusio shell receiving a circumferentially extending annular region of the acetabular cup adjacent the mouth of the acetabular cup and carried by said acetabular cup on the outer surface thereof whereby the acetabular cup and the protrusio shell can be implanted as a unit, said protrusio shell including flange means adjacent one end of the protrusio shell projecting generally radially outwardly and adapted to engage the rim of the acetabulum; and
said outer surface of the acetabular cup having a circumferentially extending groove which receives at least a portion of the protrusio shell, said groove extending in the circumferential direction of said annular region.

18. A protrusio cup as defined in claim 17 wherein said flange means includes first and second circumferentially spaced flanges projecting outwardly from the portion of said acetabular cup which defines said bearing surface extension.

* * * * *